(12) United States Patent
Ternes et al.

(10) Patent No.: US 8,706,212 B2
(45) Date of Patent: Apr. 22, 2014

(54) NEURAL STIMULATION SYSTEMS, DEVICES AND METHODS

(75) Inventors: David Ternes, Roseville, MN (US); Andrew P. Kramer, Stillwater, MN (US); Imad Libbus, St. Paul, MN (US); Jeffrey E. Stahmann, Ramsey, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1454 days.

(21) Appl. No.: 11/610,234

(22) Filed: Dec. 13, 2006

(65) Prior Publication Data

US 2008/0147140 A1    Jun. 19, 2008

(51) Int. Cl.
*A61N 1/362* (2006.01)

(52) U.S. Cl.
USPC .............................................................. 607/2

(58) Field of Classification Search
USPC .............................................................. 607/2
See application file for complete search history.

(56) References Cited

U.S. PATENT DOCUMENTS

| | | | |
|---|---|---|---|
| 4,327,322 A | 4/1982 | Yukl | |
| 4,887,603 A | 12/1989 | Morawetz et al. | |
| 5,397,338 A | 3/1995 | Grey et al. | |
| 5,512,057 A | 4/1996 | Reiss et al. | |
| 5,522,854 A | 6/1996 | Ideker et al. | |
| 5,792,187 A | 8/1998 | Adams | |
| 6,167,305 A | 12/2000 | Cammilli et al. | |
| 6,400,982 B2 | 6/2002 | Sweeney et al. | |
| 6,463,328 B1 | 10/2002 | John | |
| 6,466,822 B1 | 10/2002 | Pless | |
| 7,039,466 B1 | 5/2006 | Harrison et al. | |
| 2003/0004549 A1* | 1/2003 | Hill et al. | 607/9 |
| 2004/0002635 A1 | 1/2004 | Hargrove et al. | |
| 2005/0020909 A1 | 1/2005 | Moctezuma de la Barrera et al. | |
| 2005/0149127 A1 | 7/2005 | Libbus | |
| 2006/0020297 A1 | 1/2006 | Gerber et al. | |
| 2006/0142822 A1 | 6/2006 | Tulgar | |
| 2006/0161210 A1 | 7/2006 | Pastore et al. | |
| 2006/0195152 A1 | 8/2006 | Gerber | |
| 2006/0253157 A1 | 11/2006 | Libbus et al. | |
| 2006/0253161 A1 | 11/2006 | Libbus et al. | |
| 2006/0271118 A1 | 11/2006 | Libbus et al. | |
| 2006/0287681 A1 | 12/2006 | Yonce et al. | |
| 2007/0100380 A1 | 5/2007 | Fukui | |
| 2007/0142864 A1 | 6/2007 | Libbus et al. | |
| 2007/0156198 A1 | 7/2007 | Rossing et al. | |
| 2007/0260283 A1 | 11/2007 | Li | |
| 2007/0288070 A1 | 12/2007 | Libbus et al. | |
| 2008/0004672 A1 | 1/2008 | Dalal et al. | |
| 2009/0198294 A1 | 8/2009 | Rossing et al. | |

FOREIGN PATENT DOCUMENTS

WO    WO-2008073235 A1    6/2008

OTHER PUBLICATIONS

Libbus, I., et al., "System for Neurally-Mediated Anti-Arrhythmic Therapy", U.S. Appl. No. 11/538,488, filed Oct. 4, 2006, 37 pgs.

(Continued)

*Primary Examiner* — Eric D. Bertram
(74) *Attorney, Agent, or Firm* — Schwegman Lundberg & Woessner, P.A.

(57) ABSTRACT

Various system embodiments comprise circuitry to determine when an arrhythmia has terminated, and a neural stimulator adapted to temporarily deliver a neural stimulation therapy to assist with recovering from the arrhythmia in response to termination of the arrhythmia.

19 Claims, 12 Drawing Sheets

(56) References Cited

OTHER PUBLICATIONS

PCT Application No. PCT/US2007/024756, International Search Report mailed Apr. 16, 2008, 4 pgs.

PCT Application No. PCT/US2007/024756, Written Opinion mailed Apr. 16, 2008, 7 pgs.

U.S. Appl. No. 12/422,147, Preliminary Statement filed Apr. 10, 2009, 2 pgs.

* cited by examiner

NEURAL STIMULATION SYSTEMS, DEVICES AND METHODS

FIELD

This application relates generally to medical devices and, more particularly, to systems, devices and methods for providing neural stimulation therapy.

BACKGROUND

Neural stimulation has been the subject of a number of studies and has been proposed for several therapies. Direct electrical stimulation of parasympathetic nerves can activate the baroreflex, inducing a reduction of sympathetic nerve activity and reducing blood pressure by decreasing vascular resistance. Sympathetic inhibition, as well as parasympathetic activation, have been associated with reduced arrhythmia vulnerability following a myocardial infarction, presumably by increasing collateral perfusion of the acutely ischemic myocardium and decreasing myocardial damage. Modulation of the sympathetic and parasympathetic nervous system with neural stimulation has been shown to have positive clinical benefits, such as protecting the myocardium from further remodeling and predisposition to fatal arrhythmias following a myocardial infarction.

SUMMARY

Various system embodiments comprise circuitry to determine when an arrhythmia has terminated, and a neural stimulator adapted to temporarily deliver a neural stimulation therapy to assist with recovering from the arrhythmia in response to termination of the arrhythmia. Various method embodiments comprise determining that an arrhythmia has terminated and temporarily delivering a neural stimulation therapy to assist with recovering from the arrhythmia upon termination of the arrhythmia. Various method embodiments comprise chronically performing a prophylactic neural stimulation therapy, temporarily delivering an arrhythmia therapy, an apnea therapy, or a pain therapy in response to a therapy trigger, and chronically performing the prophylactic neural stimulation therapy upon completion of the arrhythmia therapy, the apnea therapy or the pain therapy. Various method embodiments comprise delivering a pretherapy stimulation in preparation for delivering a therapy in response to a therapy trigger, delivering the therapy, and delivering a post-therapy neural stimulation to assist with recovering from the therapy upon completion of delivering of the therapy.

This Summary is an overview of some of the teachings of the present application and not intended to be an exclusive or exhaustive treatment of the present subject matter. Further details about the present subject matter are found in the detailed description and appended claims. Other aspects will be apparent to persons skilled in the art upon reading and understanding the following detailed description and viewing the drawings that form a part thereof, each of which are not to be taken in a limiting sense. The scope of the present invention is defined by the appended claims and their equivalents.

DETAILED DESCRIPTION

Figure 1:
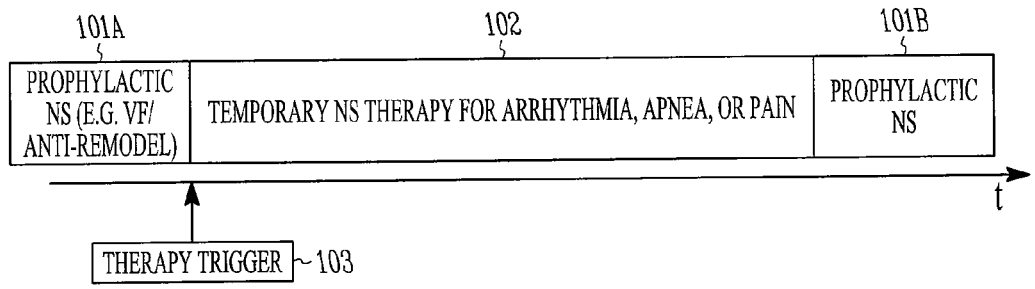
FIG. 1 illustrates a therapy time line where prophylactic neural stimulation is interrupted for a temporary neural stimulation therapy, according to various embodiments.

The following detailed description of the present subject matter refers to the accompanying drawings which show, by way of illustration, specific aspects and embodiments in which the present subject matter may be practiced. These embodiments are described in sufficient detail to enable those skilled in the art to practice the present subject matter. Other embodiments may be utilized and structural, logical, and electrical changes may be made without departing from the scope of the present subject matter. References to "an", "one", or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

Various neural stimulation device embodiments switch between or among neural stimulation modes upon an internal and/or external trigger. Different neural stimulation modes are distinct from each other in one or more ways, such as different stimulation signal amplitudes, different stimulation frequencies, different pulse widths, different duty cycles, different directionality (unidirectional in afferent direction, unidirectional in efferent direction, or bidirectional in both afferent and efferent directions), different neural stimulation schedules, different neural stimulation duration, different stimulation location(s), and/or different feedback parameter(s) for closed-loop system embodiments.

Various embodiments switch modes for a transitory period of time in response to the application of a defibrillatory shock or in response to another temporary condition such as an atrial or ventricular arrhythmia (including tachycardia or bradycardia), or apnea, or pain (including prophylactic or preventative neural stimulation such as stimulation for anticipated pain associated with an antitachycardia shock, or therapeutic stimulation such as stimulation for migraine or angina pain).

As some embodiments pertain to therapies associated with antitachycardia shocks, a brief discussion of tachycardia is provided herein. The heart is the center of a person's circulatory system. The left portions of the heart draw oxygenated blood from the lungs and pump it to the organs of the body to provide the organs with their metabolic needs for oxygen. The right portions of the heart draw deoxygenated blood from the body organs and pump it to the lungs where the blood gets oxygenated. Contractions of the myocardium provide these pumping functions. In a normal heart, the sinoatrial node, the heart's natural pacemaker, generates electrical impulses that propagate through an electrical conduction system to various regions of the heart to excite the myocardial tissues of these regions. Coordinated delays in the propagations of the electrical impulses in a normal electrical conduction system cause the various portions of the heart to contract in synchrony, which efficiently pumps the blood. Blocked or abnormal electrical conduction or deteriorated myocardial tissue causes dysynchronous contraction of the heart, resulting in poor hemodynamic performance, including a diminished blood supply to the heart and the rest of the body. Heart failure occurs when the heart fails to pump enough blood to meet the body's metabolic needs. Tachyarrhythmias are abnormal heart rhythms characterized by a rapid heart rate. Examples of tachyarrhythmias include supraventricular tachycardias (SVT's) such as atrial tachycardia (AT) and atrial fibrillation (AF), and the more dangerous ventricular tachyarrhythmias which include ventricular tachycardia (VT) and ventricular fibrillation (VF). Abnormal ventricular rhythms occur when re-entry of a depolarizing wavefront in areas of the ventricular myocardium with different conduction characteristics becomes self-sustaining or when an excitatory focus in the ventricle usurps control of the heart rate from the sinoatrial node. The result is rapid and ineffective contraction of the ventricles out of electromechanical synchrony with the atria. Many abnormal ventricular rhythms exhibit an abnormal QRS complex in an electrocardiogram because the depolarization spreads from the excitatory focus or point of re-entry directly into the myocardium rather than through the normal ventricular conduction system. Ventricular tachycardia is typically characterized by distorted QRS complexes that occur at a rapid rate, while ventricular fibrillation is diagnosed when the ventricle depolarizes in a chaotic fashion with no identifiable QRS complexes. Both ventricular tachycardia and ventricular fibrillation are hemodynamically compromising, and both can be life-threatening. Ventricular fibrillation, however, causes circulatory arrest within seconds and is the most common cause of sudden cardiac death. Cardioversion, an electrical shock delivered to the heart synchronously with the QRS complex, and defibrillation, an electrical shock delivered without synchronization to the QRS complex, can be used to terminate most tachyarrhythmias. Cardioversion and defibrillation are referred generally herein as antitachycardia shocks. The electric shock terminates the tachyarrhythmia by simultaneously depolarizing the myocardium and rendering it refractory. A class of cardiac rhythm management (CRM) devices known as an implantable cardioverter defibrillator (ICD) provides this kind of therapy by delivering a shock pulse to the heart when the device detects tachyarrhythmias. One type of electrical therapy for tachycardia is antitachycardia pacing (ATP). In ventricular ATP, the ventricles are competitively paced with one or more pacing pulses in an effort to interrupt the reentrant circuit causing the tachycardia. Modern ICDs typically have ATP capability, and deliver ATP therapy or a shock pulse when a tachyarrhythmia is detected.

Various embodiments switch modes for a transitory period of time during the charge period in preparation for a shock. Neural stimulation therapy may be reduced or withdrawn during the post-shock period. Neural stimulation therapy may switch from chronic, low-duty-cycle heart failure therapy to a temporary, high-duty-cycle neural stimulation therapy for pain minimization. The mode switch trigger may occur in response to an internal trigger or in response to a detected event (such as the detection of defibrillatory energy in a stand alone neural stimulation device). Various embodiments wait an intershock period (e.g. 10 to 30 seconds) to determine that the antitachycardia shock was successful.

Various device embodiments revert back to a chronic stimulation mode after a transitory period, such as a period within a range of approximately 10 to 100 minutes, for example. The transitory period of time can be terminated by arrhythmia cessation, arrhythmia progression (e.g. VT to VF), arrhythmia cessation plus a predetermined time interval or a predetermined number of heart beats or respiration cycles, etc., arrhythmia initiation predetermined time interval or a predetermined number of heart beats or respiration cycles, etc., and/or a change in a physiological parameter (blood pressure, conduction time, catecholamine level, etc.). The time period can be based on time, a detected end to the condition, heart beats, and end of an event plus a time interval, or a trigger based on a physiologic event.

Various embodiments employ neural stimulation for treating the cardiac system in response to and after an arrhythmic event. The neural stimulation may be independent or used in conjunction with other treatments such as bradycardia pacing.

Various device embodiments are programmed and otherwise adapted to determine an arrhythmia-ending event and subsequently alter treatment of the cardiac system with neuromodulation therapy. In various embodiments, for example, a device is programmed to deliver therapies in response to detection of a post-atrial arrhythmia and withdraw therapies in response to detection of a high-voltage defibrillation shock.

The implanted device can be an independent neuromodulation therapy system, a neuromodulation therapy system cooperating with another implanted medical device, or a combined neuromodulation therapy with other functionality such as those typically found in implanted pacemakers and defibrillators. An arrhythmia-ending event can be the result of a non-sustained atrial or ventricular arrhythmia, an arrhythmia converted via drug cardioversion, an arrhythmia terminated with antitachycardia pacing, an arrhythmia terminated with an internally-applied or externally-applied high energy shock, etc. Detection of an arrhythmia-ending event can be determined via high-voltage detection circuitry, or any of a number of sensors for discriminating between arrhythmias and for determining rate.

Various embodiments deliver neural stimulation to elicit a parasympathetic response (e.g. stimulate nerve activity at a parasympathetic target and/or inhibit nerve activity at a sympathetic target). A parasympathetic response, for example, may be desired to decrease myocardial excitability.

For example, neural stimulation that elicits a parasympathetic response decreases myocardial excitability and conduction time, thereby reducing the likelihood of spontaneous recurrence after the arrhythmic-ending event. Spontaneous recurrence is a particular concern for atrial or supraventricular arrhythmias. In addition, efficacies of pacing therapies such as bradycardia pacing and atrial overdrive pacing may be improved with the decrease of myocardial excitability that results from this type of neural stimulation. High-energy antitachycardia shocks may cause major disturbances of parasympathetic and sympathetic activity. For example, shocks may cause a burst of increased sympathetic activity, which may be attributable to the pain associated with the stimulation. Such a sympathetic burst can be pro-arrhythmic, which also suggests that a parasympathetic stimulation response would be appropriate.

A patient may tend toward bardycardia after a shock, which is a reason to partially or completely withdraw parasympathetic stimulation post-shock as parasympathetic stimulation also causes the heart rate to slow. Therefore, various embodiments withdraw neural therapies, and/or employ neural therapies that manage the restoration of proper parasympathetic and sympathetic activity and heart rate in response to detection of an arrhythmia-ending event.

Various embodiments deliver neural stimulation to elicit a sympathetic response (e.g. stimulate nerve activity at a sympathetic target and/or inhibit nerve activity at a parasympathetic target). A sympathetic response, for example, may be desired to increase cardiac output.

Various embodiments use a programmable post-arrhythmia period of time that allows for multiple programmable post-arrhythmia therapies. For example, various embodiments provide post-arrhythmia neural stimulation in response to a non-sustained or self-terminating ventricular episode such as a run of PVCs which may require an increase in sympathetic tone. Various embodiments withhold neural stimulation for a brief period after detection of a high-energy defibrillation shock followed by neural stimulation for the remainder of the post-arrhythmia period. Various embodiments provide post-arrhythmia neural stimulation in conjunction with post-arrhythmia bradycardia therapies, where the post-arrhythmia neural stimulation can include the withdrawal of neural stimulation.

Various embodiments provide neural stimulation to suppress excessive sympathetic burst during and just after the shock, followed by a brief withdrawal of neural stimulation post-shock to prevent excessive bradycardia, which can be associated with a postshock state, and then followed by neural stimulation for the remainder of the post-arrhythmia period. Various embodiments define the post-arrhythmia period in terms of a predetermined duration of time. Predetermined physiologic conditions can be used to define the end of the arrhythmia. For example, any combination of one or more of the following from the atria and/or ventricles can be used to determine the end of an arrhythmia: rate, rhythm, conduction (e.g. QRS width), repolarization properties (e.g. QT interval), etc. Once a specified combination of these parameters return to normal, the post-arrhythmia period can be considered to have ended. An evoked response (see, for example, U.S. application Ser. No. 11/157,244) can also be used to determine the end of an arrhythmia. The duration can be physician determined or device determined, and the definition based on physiologic conditions can be physician determined, physician enabled, device determined or device enabled. The evoked response can by physician determined, physician enabled, device determined or device enabled.

Various embodiments deliver neural stimulation therapy in anticipation of or in synchronization to the application of a high-voltage antitachycardia shock. The neural stimulation therapy can be delivered to provide a neurally-mediated analgesia to reduce the pain associated with the shock. The antitachycardia shock can be applied to terminate atrial or ventricular tachycardias.

If neurostimulation therapy is already being applied in the patient, the stimulation parameters are switched between or among stimulation modes (e.g. low-duty-cycle heart failure therapy to high-duty-cycle pain management). Various embodiments apply neural stimulation during the tachycardia detection period and/or during ATP application in anticipation of a shock, in response to parameter(s) predictive of a shockable event (VT, T-wave alternans, pulsus alternans, etc.), in response to a command from a physician or other care-giver (e.g. a programmer command during defibrillation threshold testing), in response to ischemia detection, in response to a patient trigger (e.g. with an external magnet or communicator) as needed (e.g. in response to angina pain, or even non-cardiac pain). Where the device is responsive to a patient trigger, various device embodiments limit the application of neural stimulation (e.g. a maximum dose in a 24-hour period). A baseline maintenance dose may be applied, which can then be increased by a patient trigger.

In some embodiments, the neural stimulator and the defibrillator are separate implantable devices. The neural stimulator can receive a signal from the defibrillator in order to trigger the application of neural stimulation, or can be adapted to automatically detect the application of defibrillatory energy (from an internal or external device) and respond accordingly. In some embodiments, the device does not have intracardiac leads. Some device embodiments have subcutaneous defibrillation capabilities. Various embodiments deliver neural stimulation to treat cardiovascular disease, lower defibrillation threshold (DFT), and/or provide shock-related analgesia. If interaction is anticipated between neurally-mediated analgesia and pain medications, neural stimulation would be modulated in response to the application of pain medication. Modulation can occur in response to either a patient trigger (e.g. magnet or communicator) or a trigger from an electronic pill box, which would communicate wirelessly with the implantable device. If different neural stimulation therapies are used to lower DFT and provide shock-related analgesia, then the neural stimulation therapies can be appropriately multiplexed or synchronized. If interaction is anticipated between the neural stimulation and arrhythmia detection (by CRM components for example), the neural stimulation can be turned off or switched to a low interference mode when a potential arrhythmic situation is identified and communicated to the neural stimulator so detection can proceed without interference.

Illustrated below are therapy time lines. The time lines are not meant to be drawn to any particular scale, but rather are intended to illustrate various operational modes for various embodiments of neural stimulation systems.

FIG. 1 illustrates a therapy time line where prophylactic neural stimulation 101A and 101B is interrupted for a temporary neural stimulation therapy 102, according to various embodiments. In various embodiments, the temporary neural stimulation includes a neural stimulation therapy to treat an arrhythmia. In various embodiments, the temporary neural stimulation includes a neural stimulation therapy to treat apnea. In various embodiments, the temporary neural stimulation includes a neural stimulation therapy to treat pain, such as therapies for migraines, angina, pain associated with antitachycardia shocks, or other pain. The illustrated temporary neural stimulation therapy 102 is initiated in response to a therapy trigger 103, which can be device-initiated, physician-initiated, or patient-initiated. The prophylactic neural stimulation can be a chronic therapy such as neural stimulation to provide an anti-remodeling therapy, to control blood pressure, or to prevent or reduce the risk of cardiac arrhythmia.

Figure 2:
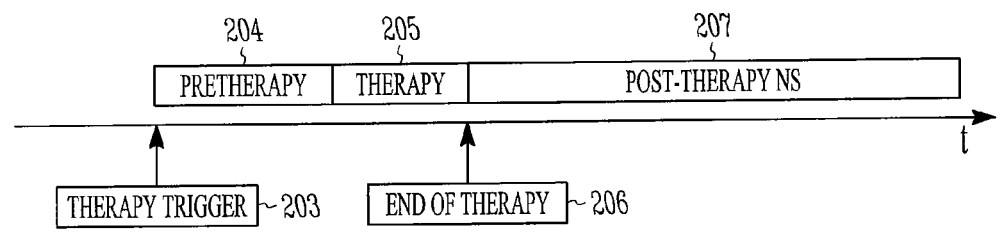
FIG. 2 illustrates a therapy time line where pre-therapy and post-therapy stimulations are delivered, according to various embodiments.

FIG. 2 illustrates a therapy time line where pre-therapy and post-therapy stimulations are delivered, according to various embodiments of the present subject matter. In various embodiments, the system delivers pretherapy 204 in response to a therapy trigger 203. An example of pretherapy includes neural stimulation to reduce pain and/or neural stimulation to lower defibrillation threshold in anticipation of an antitachycardia shock. Another example of pretherapy includes neural stimulation to change a tachycardia to make it more amenable to an antitachycardia pacing (ATP) therapy (see, for example, U.S. application Ser. No. 11/382,120, filed May 8, 2006 and entitled METHOD AND DEVICE FOR PROVIDING ANTITACHYARRHYTHMIA THERAPY, which is herein incorporated by reference). Another example of pre-therapy is turning off or adjusting the neural stimulation to avoid the neural stimulation from interfering with arrhythmia detection. After the pretherapy, the system delivers therapy 205 which, for example, can be an antitachycardia shock or antitachycardia pacing for various embodiments that treat arrhythmia. After the therapy is completed, as identified by the end of therapy trigger 206, a post-therapy neural stimulation schedule 207 is provided to assist with a physiological recovery from the therapy. In various embodiments that treat arrhythmia, the post-therapy neural stimulation schedule is provided to reduce the risk of another arrhythmia episode and/or maintain appropriate cardiac output.

Figure 3:
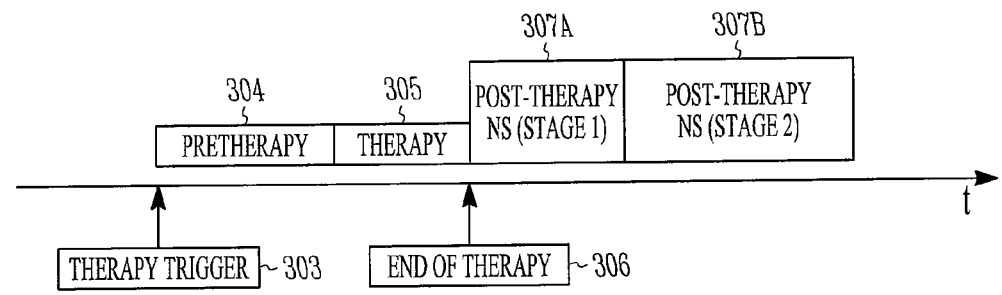
FIG. 3 illustrates a therapy time line where pre-therapy and multi-stage post-therapy stimulations are delivered, according to various embodiments.

FIG. 3 illustrates a therapy time line where pre-therapy and multi-stage post-therapy stimulations are delivered, according to various embodiments. In various embodiments, the system delivers pretherapy 304 in response to a therapy trigger 303. An example of pretherapy includes neural stimulation to reduce pain and/or neural stimulation to lower defibrillation threshold in anticipation of an antitachycardia shock. Another example of pretherapy includes neural stimulation to change a tachycardia to make it more amenable to an antitachycardia pacing (ATP) therapy. Another example of pre-therapy is turning off or adjusting the neural stimulation to avoid the neural stimulation from interfering with arrhythmia detection. After the pretherapy, the system delivers therapy 305, which, for example, can be an antitachycardia shock or antitachycardia pacing for various embodiments that treat arrhythmia. After the therapy is completed, as identified by the end of therapy trigger 306, a multistage post-therapy neural stimulation schedule is provided to assist with a physiological recovery from the therapy. The illustrated multistage post-therapy neural stimulation schedule includes a first stage 307A and a second stage 307B. Various embodiments turn the neural stimulation off during the first stage 307A.

Figure 4:
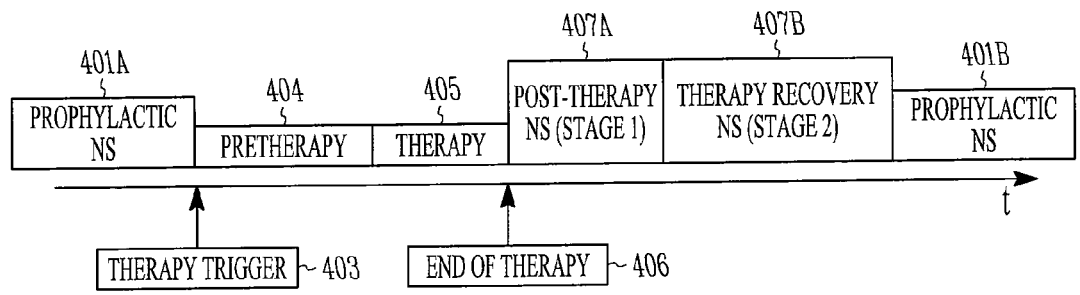
FIG. 4 illustrates a therapy time line where prophylactic neural stimulation is interrupted to provide a pre-therapy stimulation, a therapy, and a multi-stage post-therapy stimulation, according to various embodiments.

FIG. 4 illustrates a therapy time line, wherein prophylactic neural stimulation is interrupted to provide a pre-therapy stimulation, a therapy, and a multi-stage post-therapy stimulation, according to various embodiments. The time line illustrated in FIG. 4 is similar to FIG. 3, and further illustrates that prophylactic neural stimulation 401A and 401B is interrupted by pretherapy neural stimulation 404, a therapy 405, first and second stages 407A and 407B of post therapy neural stimulation. The illustrated time line indicates that the system is responsive to a therapy trigger 403 and an end of therapy trigger 406.

Figure 5:
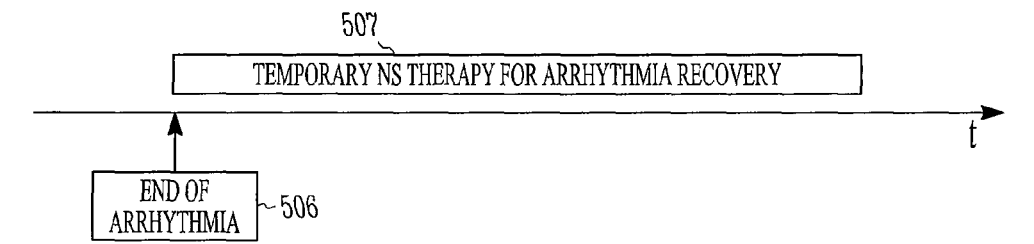
FIG. 5 illustrates a therapy time line where post-arrhythmia therapy is delivered, according to various embodiments.

FIG. 5 illustrates a therapy time line where a post-arrhythmia therapy is delivered, according to various embodiments. In the illustrated embodiment, the system responds to an end of an arrhythmia trigger 506 with a temporary neural stimulation therapy for arrhythmia recovery 507. Various embodiments detect the end of an arrhythmia by receiving a communication signal from the defibrillator indicating that a shock is being applied, or by detecting shock energy from the applied anti-tachyarrhythmia shock. Various embodiments wait an intershock period to ensure that the shock was successful and thus determine that the arrhythmia has ended. The temporary neural stimulation therapy 507 can include a time for withdrawing some or all parasympathetic stimulation to avoid encouraging a bradycardia episode after the shock, or can include applying neural stimulation to elicit some sympathetic stimulation to promote cardiac output immediately after the shock. The temporary neural stimulation therapy 507 can include neural stimulation to elicit a parasympathetic response to discourage another arrhythmic episode after the therapy is applied.

Figure 6:
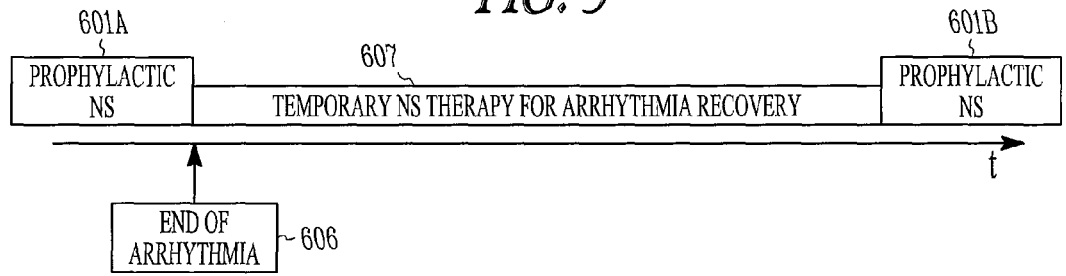
FIG. 6 illustrates a therapy time line where prophylactic neural stimulation is interrupted by post-arrhythmia therapy, according to various embodiments.

FIG. 6 illustrates a therapy time line where prophylactic neural stimulation is interrupted by post-arrhythmia therapy, according to various embodiments. The time line illustrated in FIG. 6 is similar to the time line illustrated FIG. 5, and further illustrates that prophylactic neural stimulation 601A and 601B is interrupted by an end of arrhythmia trigger 606 for the application of the temporary neural stimulation therapy 607 for arrhythmia recovery.

Figure 7:
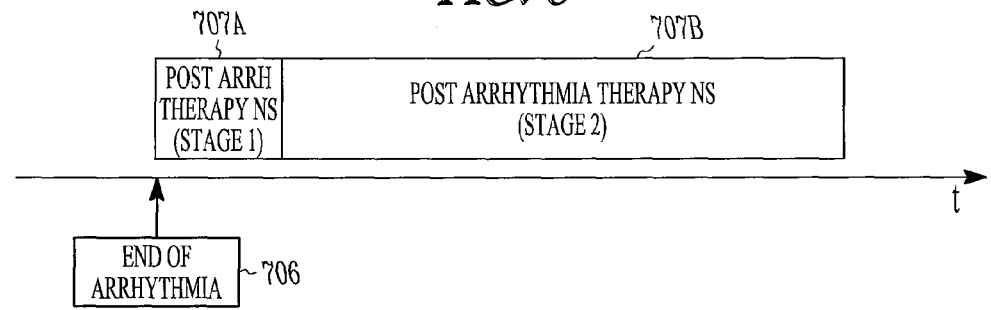
FIG. 7 illustrates a therapy time line where a multi-stage post-arrhythmia therapy is delivered, according to various embodiments.

FIG. 7 illustrates a therapy time line where a multi-stage post-arrhythmia therapy is delivered, according to various embodiments. The time line illustrated in FIG. 7 is similar to the time line illustrated in FIG. 5, and further illustrates that the neural stimulation delivered after the arrhythmia 706 includes a first stage 707A and a second stage 707B. The neural stimulation therapy, if any, in the first stage 707A after the arrhythmia is distinct from the neural stimulation therapy in the second stage 707B after the arrhythmia. Two stages are illustrated for the post-arrhythmia therapy in FIG. 7, but additional stages can be implemented as appropriate to produce the desired effects from the neural stimulation. For example, the first stage may turn off or reduce neural stimulation that elicits a parasympathetic response to prevent bradycardia, and the second stage may deliver neural stimulation to elicit a parasympathetic response to prevent re-initiation of the arrhythmia. Or, for example, the first stage may deliver neural stimulation to elicit a parasympathetic response to prevent re-initiation of the arrhythmia, and the second stage may turn off or reduce neural stimulation that elicits a parasympathetic response to prevent bradycardia.

Figure 8:
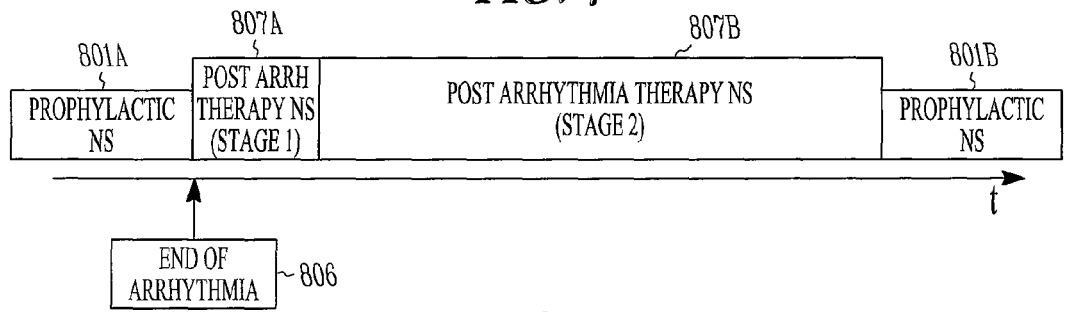
FIG. 8 illustrates a therapy time line where prophylactic neural stimulation is interrupted by multi-stage post-arrhythmia therapy, according to various embodiments.

FIG. 8 illustrates a therapy time line where prophylactic neural stimulation is interrupted by multi-stage post-arrhythmia therapy, according to various embodiments. The time line illustrated in FIG. 8 is similar to the time line illustrated FIG. 7, and further illustrates that prophylactic neural stimulation 801A and 801B is interrupted by an end of arrhythmia trigger 806 for the application of the temporary, multi-stage neural stimulation therapy 807A and 807B for arrhythmia recovery.

Figure 9:
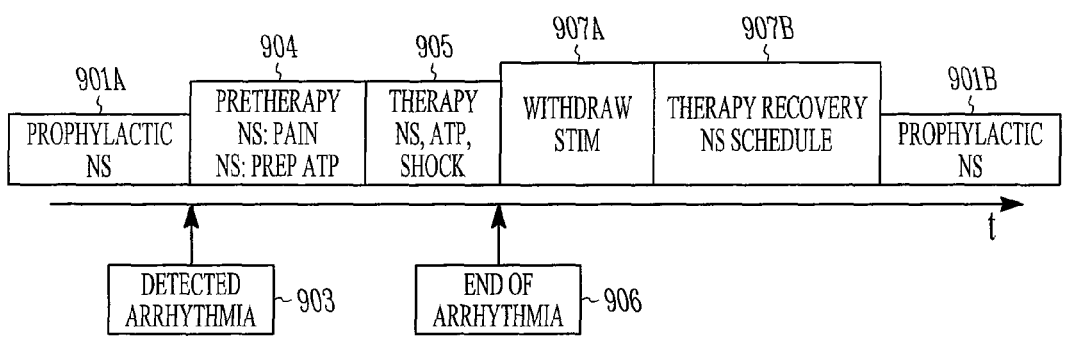
FIG. 9 illustrates a therapy time line where prophylactic neural stimulation is interrupted to deliver a pre-therapy stimulation, a therapy for an arrhythmia, and a multi-stage post arrhythmia stimulation, according to various embodiments.

FIG. 9 illustrates a therapy time line where prophylactic neural stimulation 901A and 901B is interrupted by a detected arrhythmia 903 to deliver a pre-therapy stimulation 904, a therapy 905 for an arrhythmia, and a multi-stage post arrhythmia stimulation 907A and 907B delivered after the end of the arrhythmia 906, according to various embodiments. Examples of pretherapy neural stimulation include neural stimulation to reduce pain associated with the therapy, to lower a defibrillation threshold, or to modify a tachyarrhythmia in anticipation for an antitachycardia pacing therapy. Therapies for arrhythmias can include neural stimulation to treat the arrhythmia, antitachycardia pacing, and/or antitachycardia shocks. The illustrated first stage of post-arrhythmia stimulation involves partially or completely withdrawing neural stimulation, such as stimulation that may induce a parasympathetic response after the therapy (e.g. shock) to discourage bradycardia episodes. The illustrated second stage of post-arrhythmia stimulation involves delivering neural stimulation according to a schedule to discourage another tachycardia for a period in which the heart is more vulnerable to subsequent tachycardias. The trigger indicating the end of the arrhythmia 906 can be sensed (e.g. a sensed normal sinus rhythm, a sensed antitachycardia shock plus an intershock period) or can be communicated through a communication signal. In embodiments that are capable of delivering simultaneous therapies (e.g. neural stimulation, antitachycardia pacing, and shock), the controller can be programmed to prevent the delivery of simultaneous energy discharges (see, for example, US 20060241699, entitled Neural Stimulation System To Prevent Simultaneous Energy Discharges).

Figure 10:
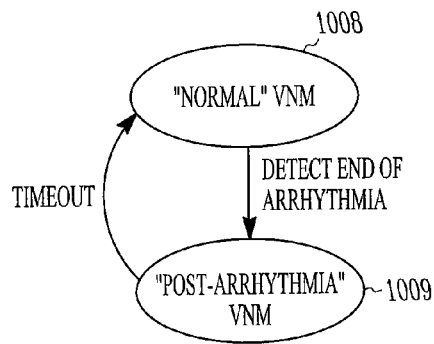
FIGS. 10-13 illustrate flow diagrams of processes for delivering post-arrhythmia vagus nerve modulation (VNM), according to various embodiments.

FIG. 10 illustrates a flow diagram of a process for delivering post-arrhythmia vagus nerve modulation (VNM), according to various embodiments. The illustrated process includes a normal or chronic VNM at 1008. After an arrhythmia has ended, the process proceeds to temporarily deliver a post-arrhythmia VNM at 1009. In the illustrated embodiment, the process returns to 1008 once a timeout is received for the post-arrhythmia VNM therapy.

Figure 11:
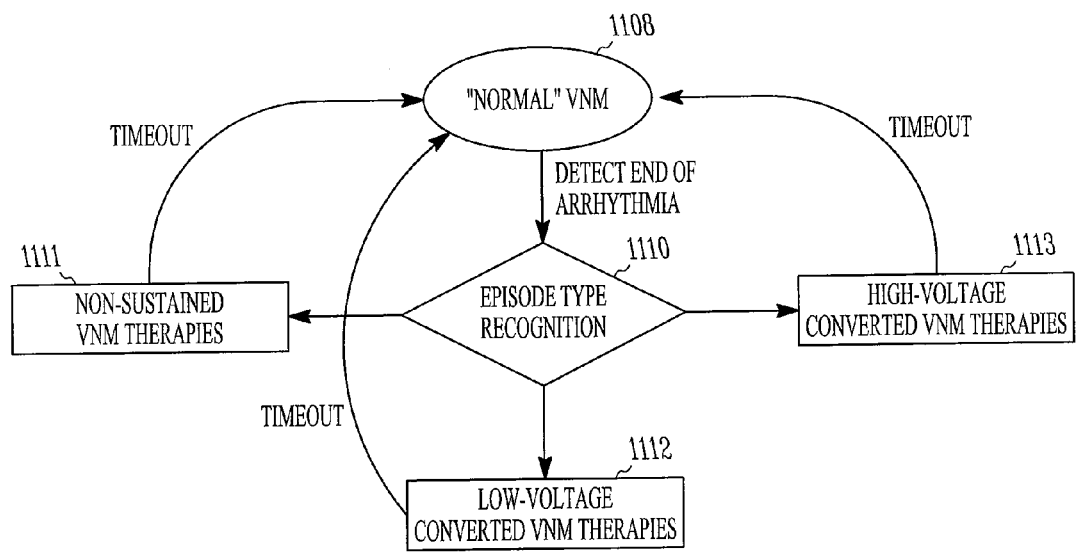

FIG. 11 illustrates a flow diagram of a process for delivering post-arrhythmia vagus nerve modulation (VNM), according to various embodiments. The illustrated process includes a normal or chronic VNM at 1108. VNM can also be referred to as vagal stimulation therapy (VST). After an arrhythmia has ended, the process proceeds to 1110 to determine how the arrhythmia terminated (e.g. a self-terminating or non-sustained arrhythmia, a low voltage terminated arrhythmia, or a high-voltage terminated arrhythmia). A VNM therapy for non-sustained or self-terminating arrhythmias is delivered at 1111, a VNM therapy for arrhythmias terminated using low voltage stimulation is delivered at 1112, and a VNM therapy for arrhythmias terminated using high-voltage stimulation shocks is delivered at 1113. After the VNM therapy, the process returns to 1108 after a timeout or terminating event, such as a communicated signal from a CRM device or a physiologic signal.

Figure 12:
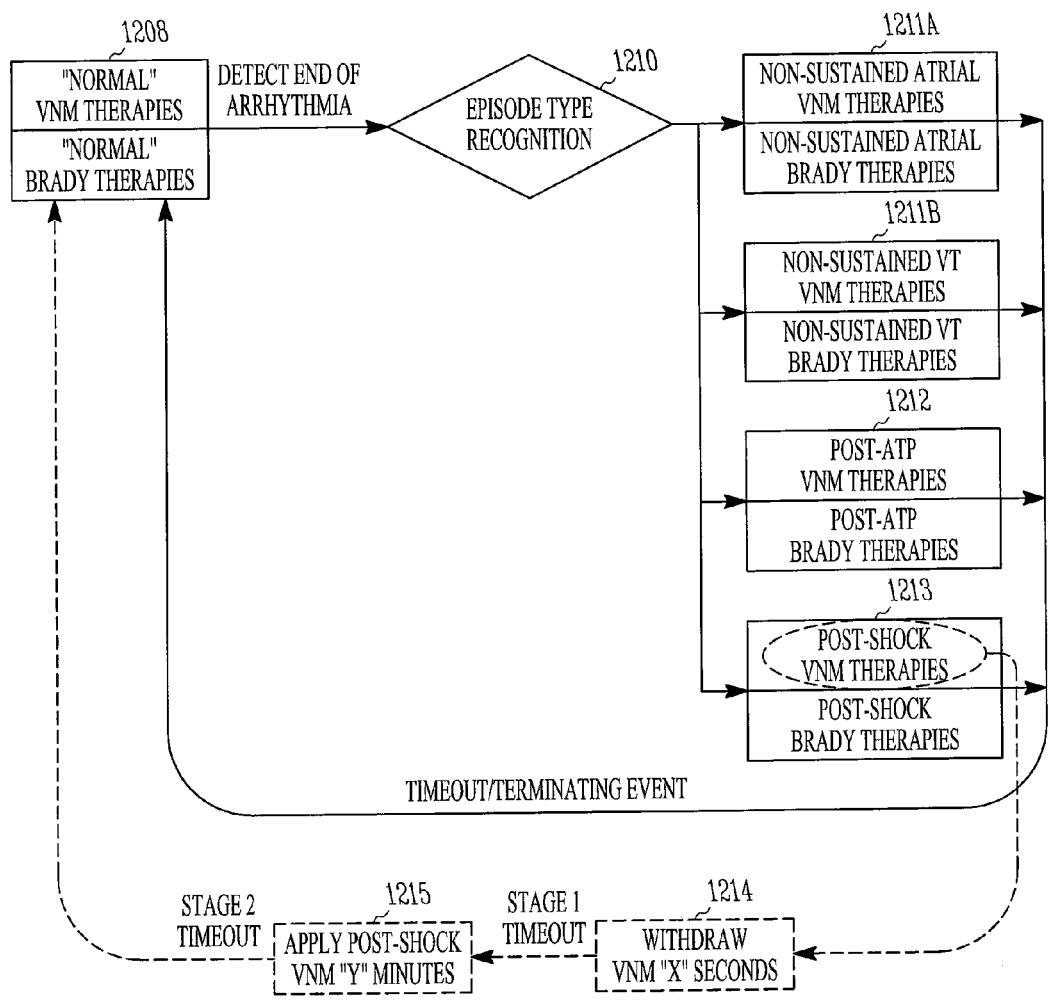

FIG. 12 illustrates a flow diagram of a process for delivering post-arrhythmia vagus nerve modulation (VNM), according to various embodiments. The illustrated process includes a normal or chronic VNM at 1208, along with normal bradycardia therapies. After an arrhythmia has ended, the process proceeds to 1210 to determine how the arrhythmia terminated (e.g. a self-terminating or non-sustained arrhythmia, a low voltage terminated arrhythmia, or a high-voltage terminated arrhythmia). A VNM therapy for non-sustained or self-terminating atrial arrhythmias is delivered at 1211A along with an atrial bradycardia therapy, and a VNM therapy for non-sustained or self-terminating ventricular tachyarrhythmias is delivered at 1211B along with a ventricular tachyarrhythmia bradycardia therapy. A VNM therapy for arrhythmias terminated using low voltage, ATP stimulation is delivered at 1212 along with post-ATP bradycardia therapies, and a VNM therapy for arrhythmias terminated using high-voltage antitachycardia stimulation shocks is delivered at 1213 along with post-shock bradycardia therapies. In response to a timeout or terminating event, normal VNM therapies can be delivered again. In the illustrated embodiment, the post-shock VNM therapies includes temporarily withdrawing VNM (e.g. for a time period on the order of seconds) at 1214 until a stage 1 timeout is received and includes applying a post-shock VNM (e.g. for a time period on the order of minutes) at 1215 until a stage 2 timeout is received, upon which time normal VNM therapies are delivered at 1208.

Figure 13:
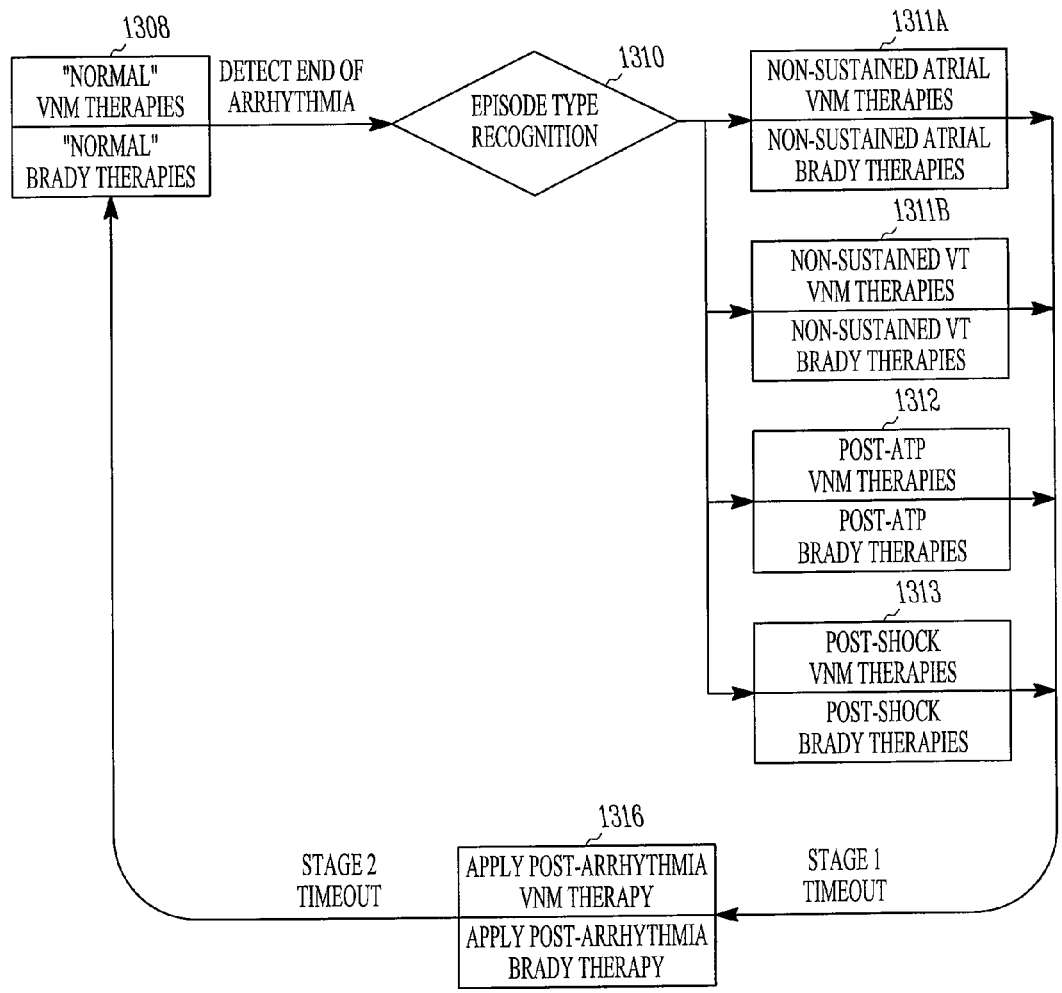

FIG. 13 illustrates a flow diagram of a process for delivering post-arrhythmia vagus nerve modulation (VNM), according to various embodiments. The illustrated process includes a normal or chronic VNM at 1308, along with normal bradycardia therapies. After an arrhythmia has ended, the process proceeds to 1310 to determine how the arrhythmia terminated (e.g. a self-terminating or non-sustained arrhythmia, a low voltage terminated arrhythmia, or a high-voltage terminated arrhythmia). A VNM therapy for non-sustained or self-terminating atrial arrhythmias is delivered at 1311A along with an atrial bradycardia therapy, and a VNM therapy for non-sustained or self-terminating ventricular tachyarrhythmias is delivered at 1311B along with a ventricular tachyarrhythmia bradycardia therapy. A VNM therapy for arrhythmias terminated using low voltage, ATP stimulation is delivered at 1312 along with post-ATP bradycardia therapies, and a VNM therapy for arrhythmias terminated using high-voltage antitachycardia stimulation shocks is delivered at 1313 along with post-shock bradycardia therapies. In the illustrated embodiment, the process responds to a stage 1 timeout by applying post-arrhythmia VNM therapy and post-arrhythmia brady therapy at 1316 until a stage 2 timeout is received, at which time normal VNM therapies and normal brady therapies are delivered at 1308.

Figure 14:
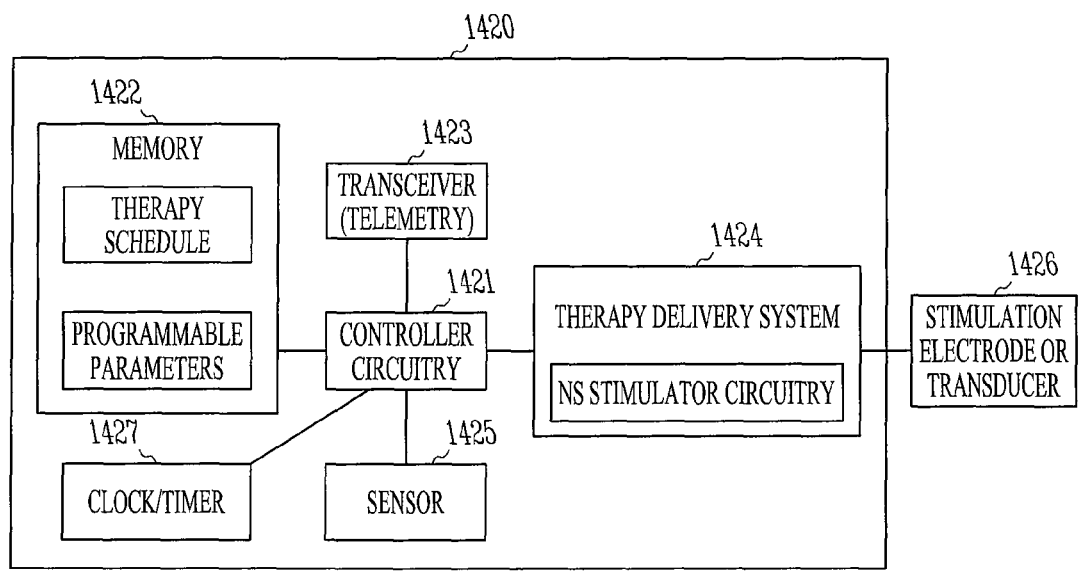
FIG. 14 illustrates an implantable medical device (IMD), according to various embodiments.

FIG. 14 illustrates an implantable medical device (IMD) 1420, according to various embodiments. The illustrated IMD 1420 provides neural stimulation signals for delivery to predetermined neural targets to provide a desired therapy. The illustrated device includes controller circuitry 1421 and memory 1422. The controller circuitry is capable of being implemented using hardware, software, and combinations of hardware and software. For example, according to various embodiments, the controller circuitry includes a processor to perform instructions embedded in the memory to perform functions associated with the neural stimulation therapy. The illustrated device further includes a transceiver 1423 and associated circuitry for use to communicate with a programmer or another external or internal device. Various embodiments have wireless communication capabilities. For example, some transceiver embodiments use a telemetry coil to wirelessly communicate with a programmer or another external or internal device.

The illustrated device further includes a therapy delivery system 1424, including neural stimulation circuitry. Various embodiments of the device also includes sensor circuitry

1425. According to some embodiments, one or more leads are able to be connected to the sensor circuitry and neural stimulation circuitry. Some embodiments use wireless connections between the sensor(s) and sensor circuitry, and some embodiments use wireless connections between the stimulator circuitry and electrodes. According to various embodiments, the neural stimulation circuitry is used to apply electrical stimulation pulses to desired neural targets, such as through one or more stimulation electrodes 1426 positioned at predetermined location(s). Some embodiments use transducers to provide other types of energy, such as ultrasound, light or magnetic energy. In various embodiments, the sensor circuitry is used to detect physiological responses. Examples of physiological responses include blood pressure, cardiac activity such as heart rate, and respiration such as tidal volume and minute ventilation. The controller circuitry can control the therapy using a therapy schedule in memory 1422 and an internal clock or timer 1427, or can compare a target range (or ranges) of the sensed physiological response(s) stored in the memory 1422 to the sensed physiological response(s) to appropriately adjust the intensity of the neural stimulation/inhibition.

According to various embodiments using neural stimulation, the stimulation circuitry 1424 is adapted to set or adjust any one or any combination of stimulation features. Examples of stimulation features include, but are not limited to, the amplitude, frequency, polarity and wave morphology of the stimulation signal. Examples of wave morphology include a square wave, triangle wave, sinusoidal wave, and waves with desired harmonic components to mimic white noise such as is indicative of naturally-occurring nerve traffic. Some embodiments of the neural stimulation circuitry 1424 are adapted to generate a stimulation signal with a predetermined amplitude, morphology, pulse width and polarity, and are further adapted to respond to a control signal from the controller to modify at least one of the amplitude, wave morphology, pulse width and polarity. Some embodiments of the neural stimulation circuitry 1424 are adapted to generate a stimulation signal with a predetermined frequency, and are further adapted to respond to a control signal from the controller to modify the frequency of the stimulation signal.

The controller 1421 can be programmed to control the neural stimulation delivered by the stimulation circuitry 1424 according to stimulation instructions, such as a stimulation schedule, stored in the memory 1422. Neural stimulation can be delivered in a stimulation burst, which is a train of stimulation pulses at a predetermined frequency. Stimulation bursts can be characterized by burst durations and burst intervals. A burst duration is the length of time that a burst lasts. A burst interval can be identified by the time between the start of successive bursts. A programmed pattern of bursts can include any combination of burst durations and burst intervals. A simple burst pattern with one burst duration and burst interval can continue periodically for a programmed period or can follow a more complicated schedule. The programmed pattern of bursts can be more complicated, composed of multiple burst durations and burst interval sequences. The programmed pattern of bursts can be characterized by a duty cycle, which refers to a repeating cycle of neural stimulation ON for a fixed time and neural stimulation OFF for a fixed time.

According to some embodiments, the controller 1421 controls the neural stimulation generated by the stimulation circuitry by initiating each pulse of the stimulation signal. In some embodiments, the controller circuitry initiates a stimulation signal pulse train, where the stimulation signal responds to a command from the controller circuitry by generating a train of pulses at a predetermined frequency and burst duration. The predetermined frequency and burst duration of the pulse train can be programmable. The pattern of pulses in the pulse train can be a simple burst pattern with one burst duration and burst interval or can follow a more complicated burst pattern with multiple burst durations and burst intervals. In some embodiments, the controller 1421 controls the stimulation circuitry 1424 to initiate a neural stimulation session and to terminate the neural stimulation session. The burst duration of the neural stimulation session under the control of the controller 1421 can be programmable. The controller may also terminate a neural stimulation session in response to an interrupt signal, such as may be generated by one or more sensed parameters or any other condition where it is determined to be desirable to stop neural stimulation.

The sensor circuitry is used to detect a physiological response. The controller 1421 compares the response to a target range stored in memory, and controls the neural stimulation based on the comparison in an attempt to keep the response within the target range. The target range can be programmable.

The illustrated device includes a clock or timer 1427 which can be used to execute the programmable stimulation schedule. For example, a physician can program a daily schedule of therapy based on the time of day. A stimulation session can begin at a first programmed time, and can end at a second programmed time. Various embodiments initiate and/or terminate a stimulation session based on a signal triggered by a user. Various embodiments use sensed data to enable and/or disable a stimulation session. The timer can control the duration of pre-therapy, therapy, post-therapy, and therapy recovery neural stimulation stages.

According to various embodiments, the schedule refers to the time intervals or period when the neural stimulation therapy is delivered. A schedule can be defined by a start time and an end time, a start time and a duration, a start time and a terminating triggering event, or an initiating triggering event and an end time, or a duration or a terminating triggering event. Various schedules deliver therapy periodically. According to various embodiments, the device is programmed with a therapy schedule before, during and/or after arrhythmias, as discussed above.

According to some examples that provide prophylactic neural stimulation, a device can be programmed with a therapy schedule to deliver therapy from midnight to 2 AM every day, or to deliver therapy for one hour every six hours, or to delivery therapy for two hours per day, or according to a more complicated timetable. Various device embodiments apply the therapy according to the programmed schedule contingent on enabling conditions, such as patient rest or sleep, low heart rate levels, and the like. The therapy schedule can also specify how the stimulation is delivered, such as continuously at the pulse frequency throughout the identified therapy period (e.g. 5 Hz pulse frequency for one hour during the delivery period), or according to a defined duty cycle during the therapy delivery period (e.g. 10 seconds per minute at 5 Hz pulse frequency for one hour per day). As illustrated by these examples, the therapy schedule is distinguishable from the duty cycle.

Figure 15:
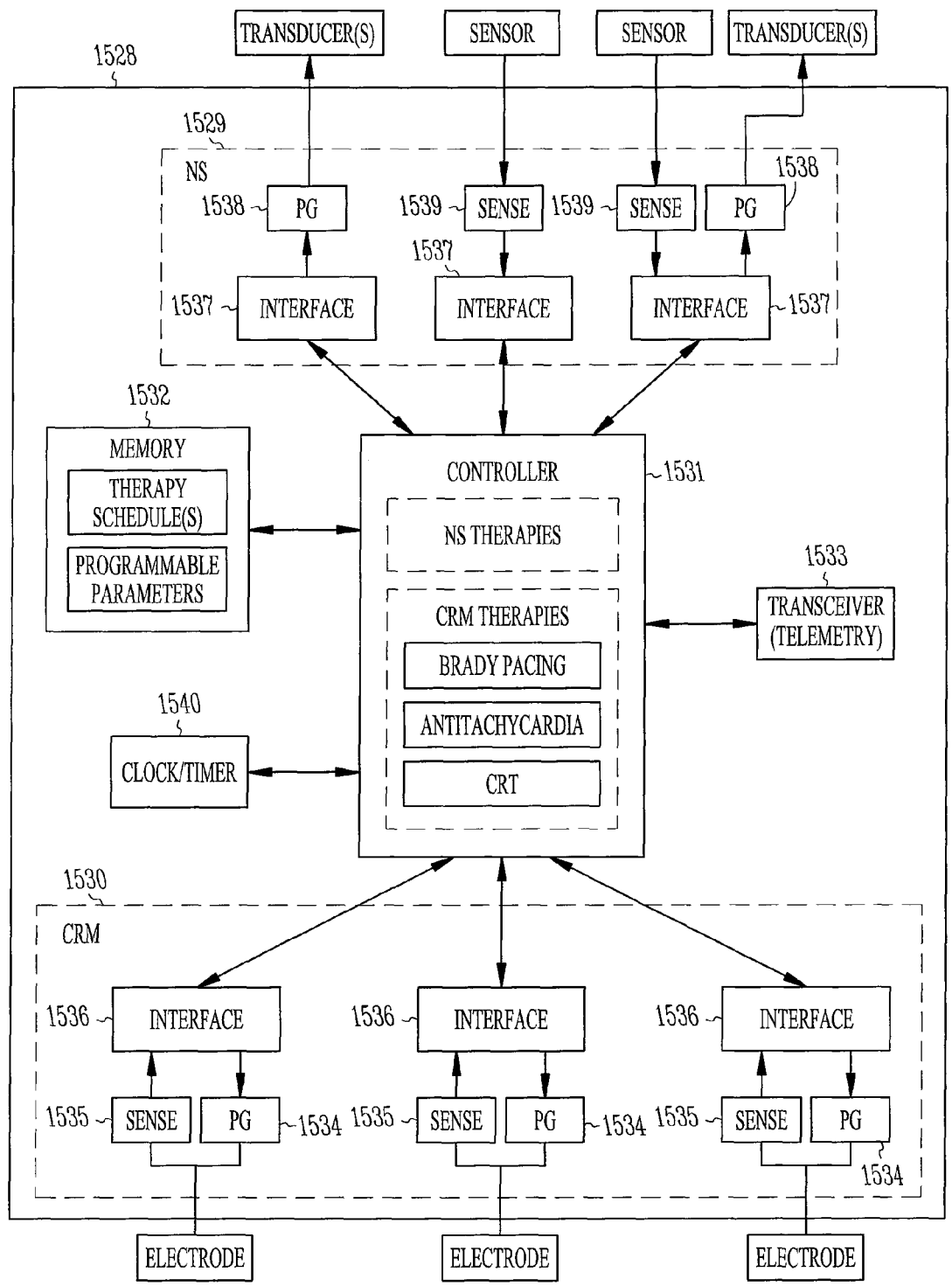
FIG. 15 illustrates an implantable medical device (IMD) having a neural stimulation (NS) component and a cardiac rhythm management (CRM) component according to various embodiments.

FIG. 15 illustrates an implantable medical device (IMD) 1528 having a neural stimulation (NS) component 1529 and a cardiac rhythm management (CRM) component 1530 according to various embodiments. The illustrated device includes a controller 1531 and memory 1532. According to various embodiments, the controller includes hardware, software, or a combination of hardware and software to perform the neural stimulation and CRM functions. For example, the programmed therapy applications discussed in this disclosure may be stored as computer-readable instructions embodied in memory and executed by a processor. For example, therapy schedule(s) and programmable parameters can be stored in memory. According to various embodiments, the controller includes a processor to execute instructions embedded in memory to perform the neural stimulation and CRM functions. Various embodiments include CRM therapies such as bradycardia pacing, antitachycardia therapies such as ATP, defibrillation and cardioversion, and cardiac resynchronization therapy (CRT). The illustrated device further includes a transceiver 1533 and associated circuitry for use to communicate with a programmer or another external or internal device. Various embodiments include a telemetry coil.

The CRM therapy section 1530 includes components, under the control of the controller, to stimulate a heart and/or sense cardiac signals using one or more electrodes. The illustrated CRM therapy section includes a pulse generator 1534 for use to provide an electrical signal through an electrode to stimulate a heart, and further includes sense circuitry 1535 to detect and process sensed cardiac signals. An interface 1536 is generally illustrated for use to communicate between the controller 1531 and the pulse generator 1534 and sense circuitry 1535. Three electrodes are illustrated as an example for use to provide CRM therapy. However, the present subject matter is not limited to a particular number of electrodes or electrode sites. Each electrode may have its own pulse generator and sense circuitry. However, the present subject matter is not so limited. A signal pulse generating and sensing function can be multiplexed to function with multiple electrodes. Additionally, an electrode can be multiplexed to function with more than one pulse generating and sensing function.

The NS therapy section 1529 includes components, under the control of the controller, to stimulate a neural stimulation target and/or sense parameters associated with nerve activity or surrogates of nerve activity such as blood pressure and respiration. Three interfaces 1537 are illustrated for use to provide neural stimulation. However, the present subject matter is not limited to a particular number interfaces, or to any particular stimulating or sensing functions. Pulse generators 1538 are used to provide electrical pulses to transducer or transducers for use to stimulate a neural stimulation target. According to various embodiments, the pulse generator includes circuitry to set, and in some embodiments change, the amplitude of the stimulation pulse, the frequency of the stimulation pulse, the burst frequency of the pulse, and the morphology of the pulse such as a square wave, triangle wave, sinusoidal wave, and waves with desired harmonic components to mimic white noise or other signals. Sense circuits 1539 are used to detect and process signals from a sensor, such as a sensor of nerve activity, heart rate, blood pressure, respiration, and the like. The interfaces 1537 are generally illustrated for use to communicate between the controller 1531 and the pulse generator 1538 and sense circuitry 1539. Each interface, for example, may be used to control a separate lead. Various embodiments of the NS therapy section only include a pulse generator to stimulate a neural target. The illustrated device further includes a clock/timer 1540, which can be used to deliver the programmed therapy according to a programmed stimulation protocol and/or schedule.

Figure 16:
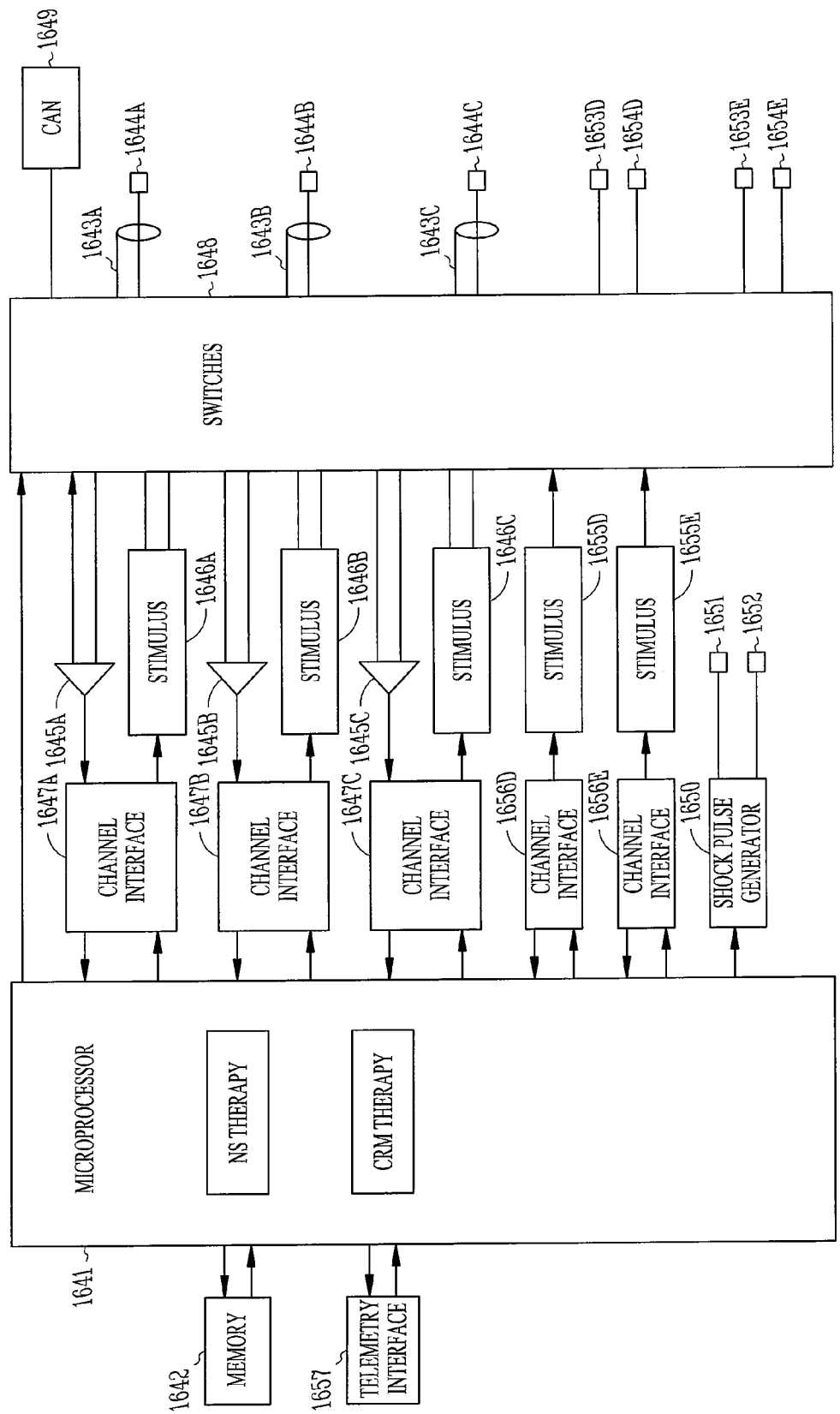
FIG. 16 shows a system diagram of an embodiment of a microprocessor-based implantable device, according to various embodiments.

FIG. 16 shows a system diagram of an embodiment of a microprocessor-based implantable device, according to various embodiments. The controller of the device is a microprocessor 1641 which communicates with a memory 1642 via a bidirectional data bus. The controller could be implemented by other types of logic circuitry (e.g., discrete components or programmable logic arrays) using a state machine type of design. As used herein, the term "circuitry" should be taken to refer to either discrete logic circuitry or to the programming of a microprocessor. Shown in the figure are three examples of sensing and pacing channels designated "A" through "C" comprising bipolar leads with ring electrodes 1643A-C and tip electrodes 1644A-C, sensing amplifiers 1645A-C, pulse generators 1646A-C, and channel interfaces 1647A-C. Each channel thus includes a pacing channel made up of the pulse generator connected to the electrode and a sensing channel made up of the sense amplifier connected to the electrode. The channel interfaces 1647A-C communicate bidirectionally with the microprocessor 1641, and each interface may include analog-to-digital converters for digitizing sensing signal inputs from the sensing amplifiers and registers that can be written to by the microprocessor in order to output pacing pulses, change the pacing pulse amplitude, and adjust the gain and threshold values for the sensing amplifiers. The sensing circuitry of the pacemaker detects a chamber sense, either an atrial sense or ventricular sense, when an electrogram signal (i.e., a voltage sensed by an electrode representing cardiac electrical activity) generated by a particular channel exceeds a specified detection threshold. Pacing algorithms used in particular pacing modes employ such senses to trigger or inhibit pacing. The intrinsic atrial and/or ventricular rates can be measured by measuring the time intervals between atrial and ventricular senses, respectively, and used to detect atrial and ventricular tachyarrhythmias.

The electrodes of each bipolar lead are connected via conductors within the lead to a switching network 1648 controlled by the microprocessor. The switching network is used to switch the electrodes to the input of a sense amplifier in order to detect intrinsic cardiac activity and to the output of a pulse generator in order to deliver a pacing pulse. The switching network also enables the device to sense or pace either in a bipolar mode using both the ring and tip electrodes of a lead or in a unipolar mode using only one of the electrodes of the lead with the device housing (can) 1649 or an electrode on another lead serving as a return electrode. A shock pulse generator 1650 is also interfaced to the controller for delivering an antitachycardia shock using shock electrodes 1651 and 1652 to the atria or ventricles upon detection of a shockable tachyarrhythmia.

Neural stimulation channels, identified as channels D and E, are incorporated into the device for delivering neural stimulation to elicit a parasympathetic response (stimulate parasympathetic traffic and/or inhibit sympathetic traffic) and/or neural stimulation to elicit a sympathetic response (stimulate sympathetic traffic and/or inhibit parasympathetic traffic), where one illustrated channel includes a bipolar lead with a first electrode 1653D and a second electrode 1654D, a pulse generator 1655D, and a channel interface 1656D, and the other illustrated channel includes a bipolar lead with a first electrode 1653E and a second electrode 1654E, a pulse generator 1655E, and a channel interface 1656E. Other embodiments may use unipolar leads in which case the neural stimulation pulses are referenced to the can or another electrode. The pulse generator for each channel outputs a train of neural stimulation pulses which may be varied by the controller as to amplitude, frequency, duty-cycle, and the like. In this embodiment, each of the neural stimulation channels uses a lead which can be intravascularly disposed near an appropriate neural target. Other types of leads and/or electrodes may also be employed. A nerve cuff electrode may be used in place of an intravascularly disposed electrode to provide neural stimulation. In some embodiments, the leads of the neural stimulation electrodes are replaced by wireless links. The figure illustrates a telemetry interface 1657 connected to the microprocessor, which can be used to communicate with an external device. The illustrated microprocessor 1641 is capable of performing neural stimulation (NS) therapy routines and myocardial (CRM) stimulation routines.

Figure 17:
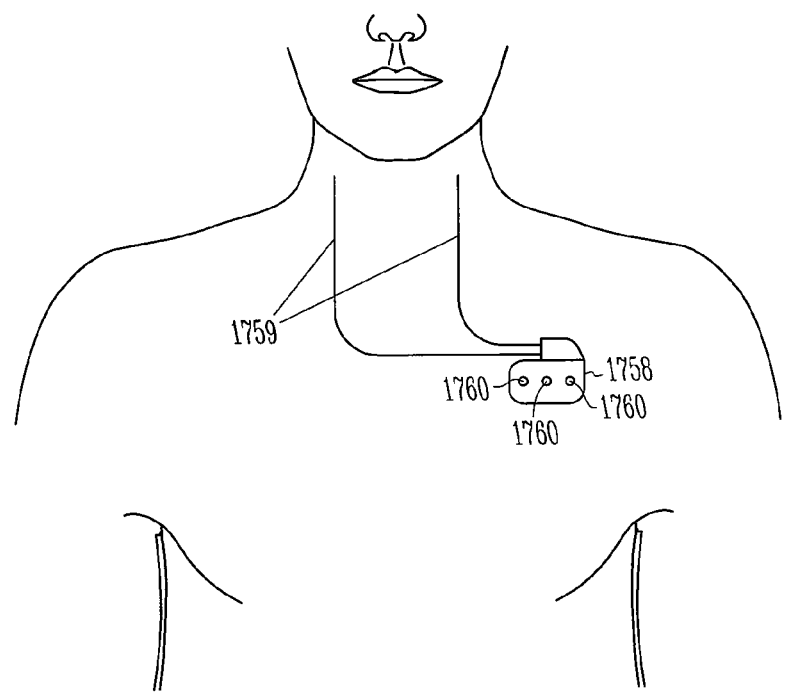
FIG. 17 illustrates a system embodiment in which an IMD is placed subcutaneously or submuscularly in a patient's chest with lead(s) positioned to stimulate a vagus nerve.

FIG. 17 illustrates a system embodiment in which an IMD 1758 is placed subcutaneously or submuscularly in a patient's chest with a lead 1759 positioned to stimulate a vagus nerve. According to various embodiments, the neural stimulation lead 1759 is subcutaneously tunneled to a neural target, and has a nerve cuff electrode to stimulate the neural target. Some vagus nerve stimulation lead embodiments are intravascularly fed into a vessel proximate to the neural target, and use electrode(s) within the vessel to transvascularly stimulate the neural target. For example, some embodiments stimulate the vagus using electrode(s) positioned within the internal jugular vein. Other embodiments deliver neural stimulation to the neural target from within the trachea, the laryngeal branches of the internal jugular vein, and the subclavian vein. The neural targets can be stimulated using other energy waveforms, such as ultrasound and light energy waveforms. Other neural targets can be stimulated, such as baroreceptors, cardiac nerves and cardiac fat pads. The illustrated system includes leadless ECG electrodes on the housing of the device. These ECG electrodes 1760 are capable of being used to detect heart rate, a specific arrhythmic episode, or arrhythmia treatment, for example.

Figure 18:
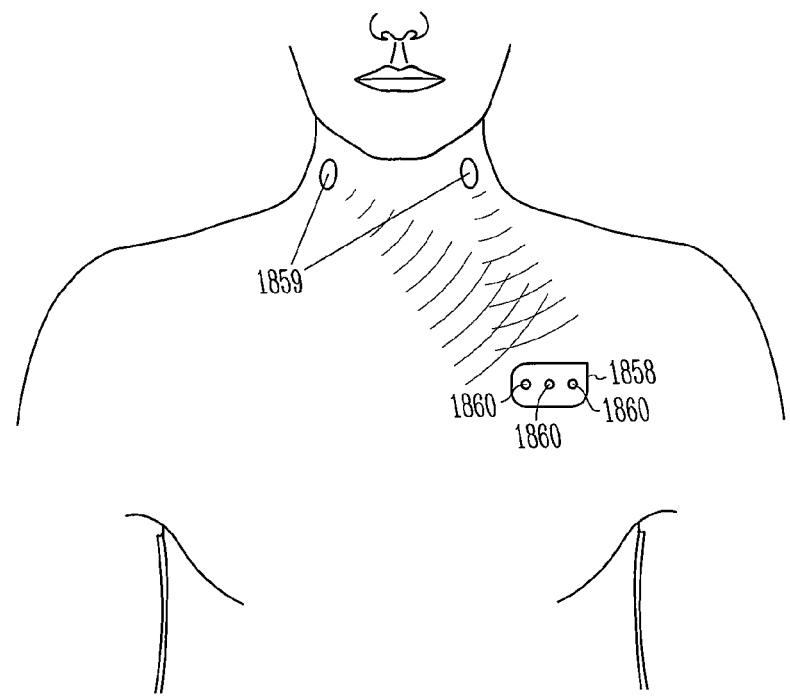
FIG. 18 illustrates a system embodiment that includes an implantable medical device (IMD) with satellite electrode(s) positioned to stimulate at least one neural target.

FIG. 18 illustrates a system embodiment that includes an implantable medical device (IMD) 1858 with satellite electrode(s) 1859 positioned to stimulate at least one neural target. The satellite electrode(s) are connected to the IMD, which functions as the planet for the satellites, via a wireless link. Stimulation and communication can be performed through the wireless link. Examples of wireless links include RF links and ultrasound links. Examples of satellite electrodes include subcutaneous electrodes, nerve cuff electrodes and intravascular electrodes. Various embodiments include satellite neural stimulation transducers used to generate neural stimulation waveforms such as ultrasound and light waveforms. The illustrated system includes leadless ECG electrodes on the housing of the device. These ECG electrodes 1860 are capable of being used to detect heart rate, a specific arrhythmic episode or arrhythmia treatment, for example.

Figure 19:
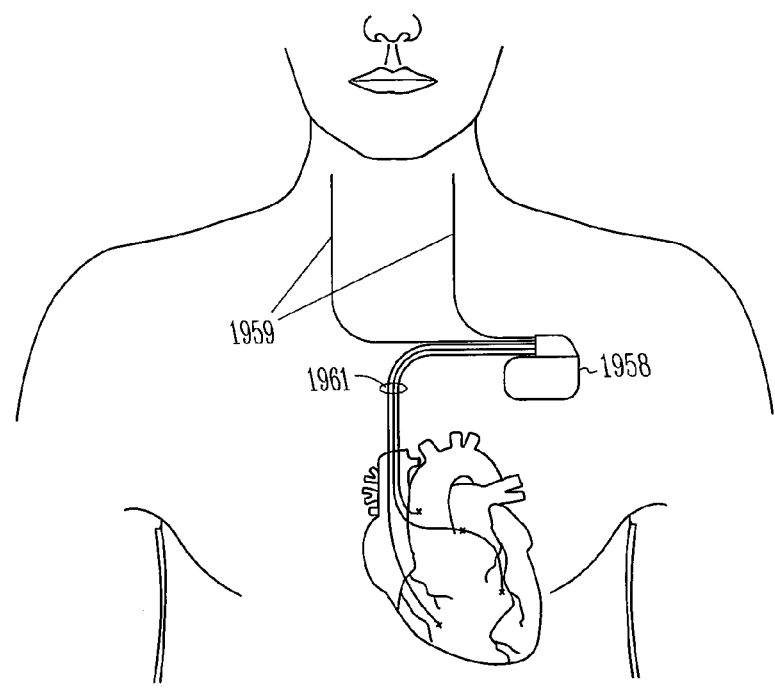
FIG. 19 illustrates an IMD placed subcutaneously or submuscularly in a patient's chest with lead(s) positioned to provide a CRM therapy to a heart, and with lead(s) positioned to stimulate and/or inhibit neural traffic at a neural target, such as a vagus nerve, according to various embodiments.

FIG. 19 illustrates an IMD 1958 placed subcutaneously or submuscularly in a patient's chest with lead(s) 1961 positioned to provide a CRM therapy to a heart, and with a lead 1959 positioned to stimulate and/or inhibit neural traffic at a neural target, such as a vagus nerve, according to various embodiments. According to various embodiments, neural stimulation lead(s) are subcutaneously tunneled to a neural target, and can have a nerve cuff electrode to stimulate the neural target. Some lead embodiments are intravascularly fed into a vessel proximate to the neural target, and use transducer(s) within the vessel to transvascularly stimulate the neural target. For example, some embodiments target the vagus nerve using electrode(s) positioned within the internal jugular vein.

Figure 20:
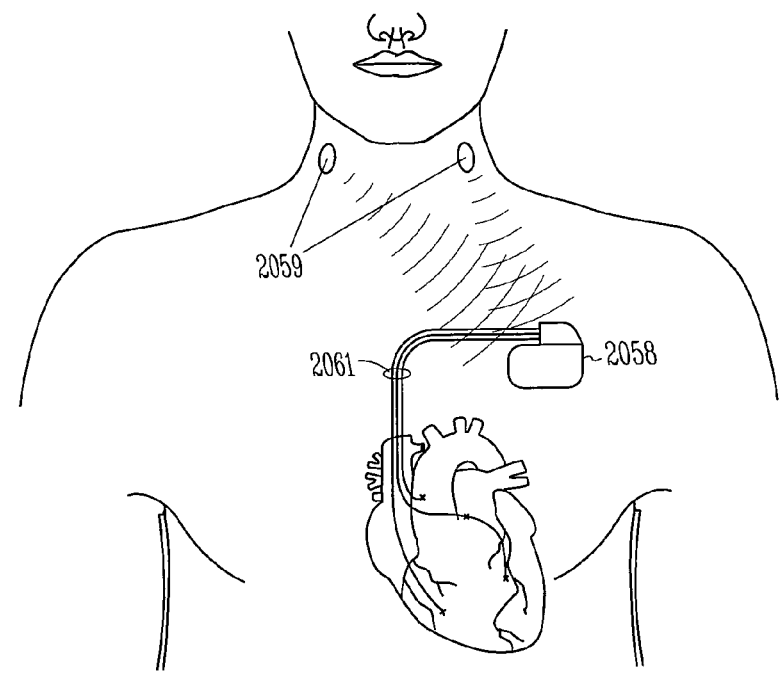
FIG. 20 illustrates an IMD with lead(s) positioned to provide a CRM therapy to a heart, and with satellite transducers positioned to stimulate/inhibit a neural target such as a vagus nerve, according to various embodiments.

FIG. 20 illustrates an IMD 2058 with lead(s) 2061 positioned to provide a CRM therapy to a heart, and with satellite transducers 2059 positioned to stimulate/inhibit a neural target such as a vagus nerve, according to various embodiments. The satellite transducers are connected to the IMD, which functions as the planet for the satellites, via a wireless link. Stimulation and communication can be performed through the wireless link. Examples of wireless links include RF links and ultrasound links. Although not illustrated, some embodiments perform myocardial stimulation using wireless links. Examples of satellite transducers include subcutaneous electrodes, nerve cuff electrodes and intravascular electrodes.

Figure 21:
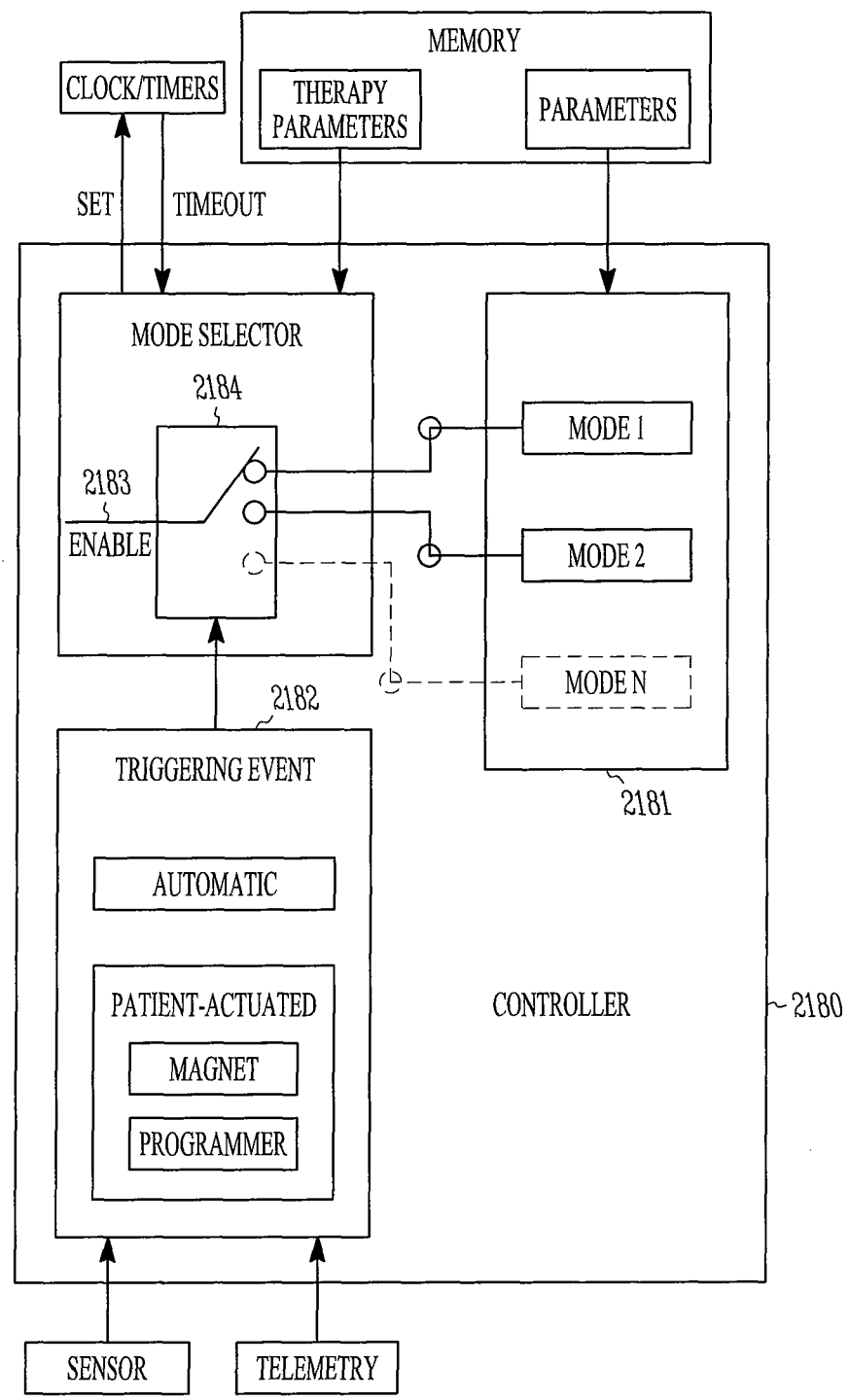
FIG. 21 illustrates an embodiment of a responsive relationship of an IMD controller to a triggering event.

FIG. 21 illustrates an embodiment of a responsive relationship of an IMD controller to a triggering event. The illustration includes a controller 2180 adapted to operate the IMD in a number of modes 2181 including a first mode, a second mode and an Nth mode. The illustration further includes a representation of a triggering event 2182, which can be an automatic event and/or a patient-actuated event such as a magnet moved proximate to a reed switch or a patient-actuated programmer. Automatic triggering events can also include a detected physiologic change such as a detected change in heart rate, a detected arrhythmia, a detected change in a respiratory rate and a detected change in blood pressure. Automatic triggering also includes detecting electrical pulses, such as high energy defibrillation shocks, trains of high frequency ATP pulses, or bradycardia therapy pacing pulses. Such pulses can be detected through, for example, leadless ECG electrodes. The illustration also includes an enable signal 2183 connected to the controller to enable a mode of operation via a switch 2184. The triggering event is adapted to control the switch to selectively enable a mode of operation by the controller. The illustrated responsive relationship can be performed in hardware, software, or a combination thereof. Sensor and/or telemetry signals can be used to provide the triggering event. The illustrated device includes a clock/timer, which can be used to receive a SET signal from the mode selector, and send a timeout signal to the mode selector after a predetermined period of time. The illustrated device also includes a memory which can include a therapy schedule for the mode selector, and parameters for the various modes.

Figure 22:
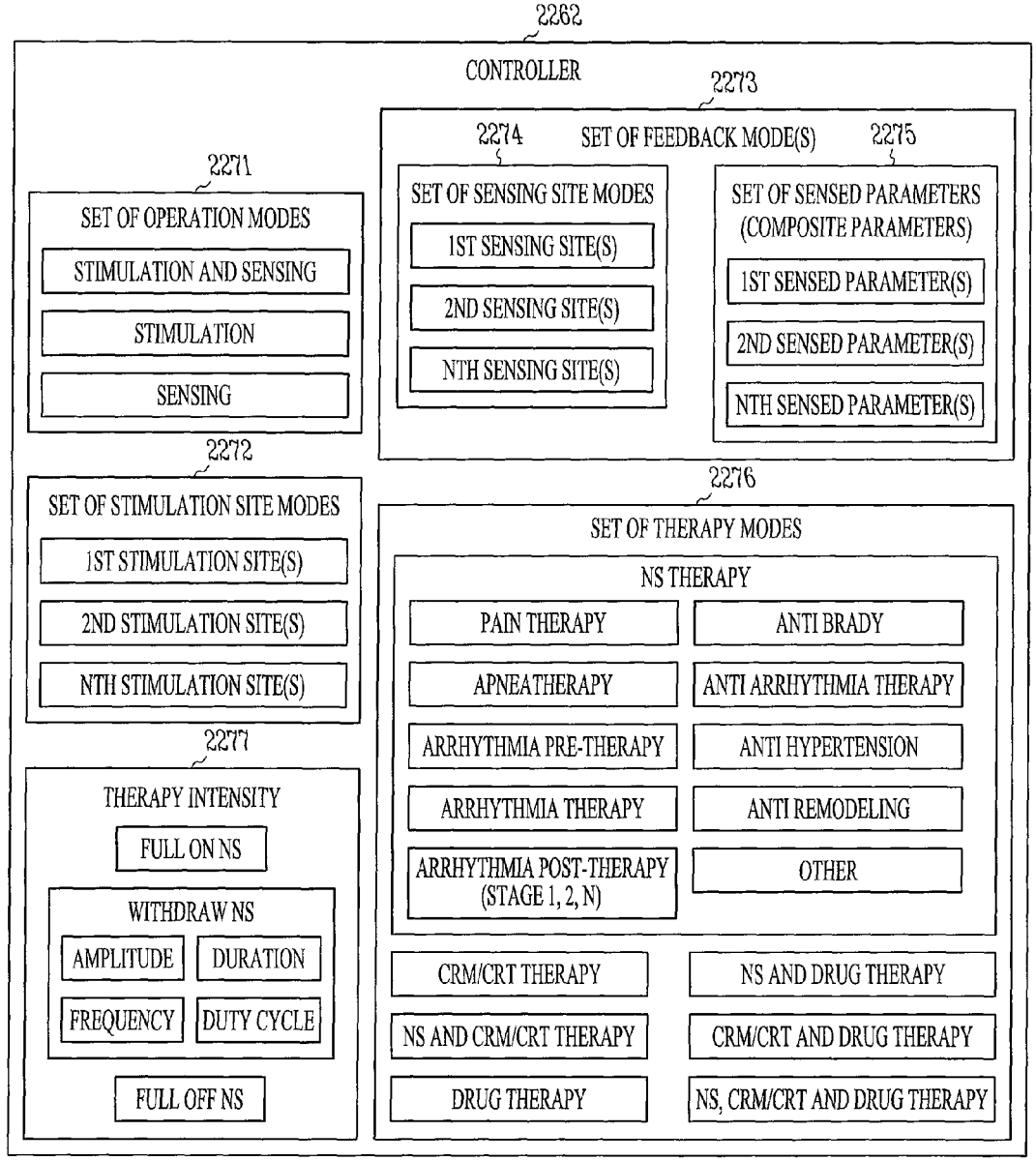
FIG. 22 illustrates an embodiment of a controller capable of switching modes within a set of operation modes, a set of stimulation site modes, and a set of feedback modes.

FIG. 22 illustrates an embodiment of a controller 2262 capable of switching modes within a set of operation modes 2271, a set of stimulation site modes 2272, and a set of feedback modes 2273. With respect to the set of operation modes, the illustrated controller is adapted to switch between or among two or more modes. Examples of modes within the set of operation modes includes a stimulation and sensing mode in which closed-loop neural stimulation is provided to neural target(s) based on sensed parameters, a stimulation mode in which open-loop neural stimulation is provided to neural target(s), and a sensing mode in which neural stimulation is not provided to neural target(s) but sensing processes continue. Examples of sensed parameters include, but are not limited to, blood pressure, heart rate, and nerve traffic.

With respect to the set of stimulation site modes, the illustrated controller 2262 is adapted to switch between or among two or more stimulation site modes. Examples of applications for switching stimulation site modes includes switching between parasympathetic and sympathetic nerve stimulation, switching from afferent to efferent stimulation, and changing the dose of the neural stimulation therapy by changing the number of stimulation sites. For example, the illustrated controller is adapted to switch among a mode to stimulate a first stimulation site or sites, a mode to stimulate a second stimulation site or sites, and a mode to stimulate an Nth stimulation site or sites. The same stimulation site can be used to inhibit or stimulate nerve traffic using different stimulation parameters, or can be used to stimulate nerve traffic in the efferent direction, in the afferent direction, or in both the efferent and afferent direction.

With respect to the set of feedback modes, the illustrated controller is adapted to switch among sensing site modes 2274 and to switch among sensed parameter and/or composite parameter modes 2275. Composite parameters are parameters based on two or more other parameters. Examples of applications for switching among sensing site modes includes recording parasympathetic or sympathetic traffic, recording afferent or efferent traffic, and switching from atrial to ventricular rhythm monitoring. Examples of applications for switching among sensed parameter/composite parameter modes include detecting short-term brief events such as an impulse burst versus a time-averaged long-term signal trend, and detecting impulse duration versus impulse magnitude. The illustrated controller is adapted to switch among a first site, a second site and an Nth site from which to provide sensing for a feedback signal, and is also adapted to switch among a first sensed parameter, a second sensed parameter and an Nth sensed parameter. Thus, although the sensing site may not change, a different parameter can be detected.

With respect to the set of therapy modes 2276, the illustrated controller is adapted to switch between or among two or more modes. Examples of modes within the set of therapy modes includes a neural stimulation therapy mode, a cardiac rhythm management and/or cardiac resynchronization therapy (CRM/CRT) mode, a neural stimulation and CRM therapy mode, a drug therapy mode, a neural stimulation and drug therapy mode, a CRM/CRT and drug therapy mode, and a neural stimulation, CRM/CRT and drug therapy mode. An example of a neural stimulation mode includes an anti-remodeling, vagal nerve stimulation therapy. An example of a CRM/CRT therapy includes a resynchronization therapy for a heart failure patient to improve the pumping function of the left ventricle. Examples of a neural stimulation and a CRM/CRT therapy include a vagal nerve stimulation therapy and antitachycardia pacing to terminate arrhythmia, and vagal nerve stimulation in anticipation of a defibrillation shock to reduce the defibrillation threshold. An example of a drug therapy mode includes an angiogenic growth factor release to treat ischemia. An example of a neural stimulation and a drug therapy mode includes vagal nerve stimulation and delivery of an angiogenic drug to promote cardiac muscle repair after an myocardial infarction. An example of a CRM/CRT and drug therapy includes pacing to unload a region of a heart damaged by a myocardial infarction such that the damaged heart region works less and delivery of an angiogenic drug to promote cardiac muscle repair. An example of a neural stimulation, CRM/CRT and drug therapy includes vagal nerve stimulation, pacing to unload a region of a heart damaged by a myocardial infarction, and delivery of an angiogenic drug to prevent post myocardial infarction remodeling. The illustrated neural stimulation therapies can be selected among pain therapy, apnea therapy, arrhythmia pre-therapy, arrhythmia therapy, arrhythmia post-therapy (stage 1, 2 . . . N), anti-bradycardia therapy, anti-arrhythmia therapy, anti-hypertension, anti-remodeling therapy, or other therapy. Therapy intensity 2277 is used to select whether the therapy is on or off, or to adjust the intensity of the therapy.

One of ordinary skill in the art will understand that, the modules and other circuitry shown and described herein can be implemented using software, hardware, and combinations of software and hardware. As such, the terms module and circuitry are intended to encompass software implementations, hardware implementations, and software and hardware implementations.

The methods illustrated in this disclosure are not intended to be exclusive of other methods within the scope of the present subject matter. Those of ordinary skill in the art will understand, upon reading and comprehending this disclosure, other methods within the scope of the present subject matter. The above-identified embodiments, and portions of the illustrated embodiments, are not necessarily mutually exclusive. These embodiments, or portions thereof, can be combined. In various embodiments, the methods are implemented using a computer data signal embodied in a carrier wave or propagated signal, that represents a sequence of instructions which, when executed by a processor cause the processor to perform the respective method. In various embodiments, the methods are implemented as a set of instructions contained on a computer-accessible medium capable of directing a processor to perform the respective method. In various embodiments, the medium is a magnetic medium, an electronic medium, or an optical medium.

It is to be understood that the above detailed description is intended to be illustrative, and not restrictive. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. A system, comprising:
   circuitry adapted to determine when an arrhythmia has terminated; and
   a neural stimulator adapted to respond to termination of the arrhythmia by initiating a programmed neural stimulation therapy, wherein the programmed neural stimulation therapy has a programmed duration and is programmed to deliver a plurality of neural stimulation pulses, and wherein the programmed neural stimulation therapy is a programmed response to the termination of the arrhythmia to assist with recovering from the arrhythmia.

2. The system of claim 1, further comprising:
   circuitry adapted to detect an arrhythmia; and
   a pulse generator to deliver an arrhythmia therapy to terminate the arrhythmia.

3. The system of claim 2, wherein the pulse generator is adapted to deliver an anti-arrhythmia shock or anti-arrhythmia pacing.

4. The system of claim 1, wherein the neural stimulator is adapted to chronically deliver a neural stimulation signal as part of a chronic therapy and temporarily deliver the programmed neural stimulation therapy to assist with recovering from the arrhythmia.

5. The system of claim 4, wherein the neural stimulator is adapted to respond to the termination of the arrhythmia by temporarily withdrawing the neural stimulation signal delivered as part of the chronic therapy.

6. The system of claim 1, further comprising an arrhythmia detector adapted to provide a signal indicative that an arrhythmia is detected, the neural stimulator being adapted to deliver a pretherapy neural stimulation signal in preparation for an arrhythmia therapy in response to the signal indicative that the arrhythmia is detected.

7. The system of claim 6, wherein the arrhythmia therapy includes an anti-arrhythmia shock therapy, and the pretherapy neural stimulation signal includes a neural stimulation therapy to reduce pain associated with the antiarrhythmia shock therapy.

8. The system of claim 6, wherein the arrhythmia therapy includes an anti-arrhythmia shock therapy, and the pretherapy neural stimulation signal includes a neural stimulation therapy to lower a defibrillation threshold.

9. The system of claim 6, wherein the arrhythmia therapy includes an antitachycardia pacing, and the pretherapy neural stimulation signal includes a neural stimulation therapy to modify the arrhythmia in preparation for antitachycardia pacing.

10. The system of claim 1, wherein the circuitry adapted to determine when the arrhythmia has terminated includes circuitry adapted to sense a delivered anti-arrhythmia shock.

11. The system of claim 1, wherein the circuitry adapted to determine when the arrhythmia has terminated includes communication circuitry adapted to receive a communication signal indicating that the arrhythmia has been terminated.

12. The system of claim 1, wherein the circuitry adapted to determine when the arrhythmia has terminated includes circuitry adapted to sense arrhythmic episodes, and sense the termination of non-sustained or self-terminating arrhythmias.

13. A method, comprising:
   determining that an arrhythmia has terminated; and
   upon termination of the arrhythmia, initiating a programmed neural stimulation therapy, wherein the programmed neural stimulation therapy has a programmed duration and is programmed to deliver a plurality of neural stimulation pulses, and wherein the programmed neural stimulation therapy is a programmed response to the termination of the arrhythmia to assist with recovering from the arrhythmia.

14. The method of claim 13, further comprising chronically performing a prophylactic neural stimulation therapy before the programmed neural stimulation therapy to assist with recovering from the arrhythmia, or after the programmed neural stimulation therapy to assist with recovering from the arrhythmia, or before and after the programmed neural stimulation therapy to assist with recovering from the arrhythmia.

15. The method of claim 13, wherein initiating the programmed neural stimulation therapy includes initiating at least a two stage neural stimulation therapy.

16. The method of claim 15, wherein the at least the two stage neural stimulation therapy includes one stage programmed to withdraw neural stimulation after arrhythmia termination, and a subsequent stage programmed to deliver neural stimulation.

17. The method of claim 13, further comprising delivering pretherapy neural stimulation in preparation for an arrhythmia therapy.

18. The method of claim 13, further comprising:
   chronically performing a prophylactic neural stimulation therapy;
   detecting an arrhythmia;
   upon detecting the arrhythmia, delivering pretherapy neural stimulation in preparation for an arrhythmia therapy;
   delivering the arrhythmia therapy;
   upon arrhythmia termination, initiating and temporarily delivering the programmed neural stimulation therapy to assist with recovering from the arrhythmia; and
   chronically performing the prophylactic neural stimulation therapy after temporarily delivering the neural stimulation therapy to assist with recovering from the arrhythmia.

19. The method of claim 18, wherein delivering pretherapy neural stimulation includes delivering neural stimulation in anticipation of pain associated with the arrhythmia therapy or to lower a defibrillation threshold when the arrhythmia therapy includes an antitachycardia shock, or includes delivering neural stimulation to make an arrhythmia more amenable to an antitachycardia pacing (ATP) therapy.

\* \* \* \* \*